United States Patent [19]

Smith

[11] Patent Number: 5,514,152

[45] Date of Patent: May 7, 1996

[54] MULTIPLE SEGMENT ENCAPSULATED MEDICAL LANCING DEVICE

[75] Inventor: Roger E. Smith, Bountiful, Utah

[73] Assignee: Specialized Health Products, Inc., Bountiful, Utah

[21] Appl. No.: 291,234

[22] Filed: Aug. 16, 1994

[51] Int. Cl.$^6$ .................................................. A61B 17/32
[52] U.S. Cl. ........................................................ 606/182
[58] Field of Search .................................. 606/181, 182, 606/183; 128/751

[56] References Cited

U.S. PATENT DOCUMENTS

| | | | |
|---|---|---|---|
| 4,627,445 | 12/1986 | Garcia | 128/770 |
| 4,637,403 | 1/1987 | Garcia | 128/770 |
| 4,995,402 | 2/1991 | Smith et al. | 606/182 |
| 5,047,044 | 9/1991 | Smith et al. | 606/182 |

FOREIGN PATENT DOCUMENTS

| | | | |
|---|---|---|---|
| 0365196 | 4/1990 | European Pat. Off. | 606/181 |

OTHER PUBLICATIONS

Turner & R. R. Holman, "Automatic Lancet for Capillary Blood Sampling", *The Lancet*, Sep. 30, 1978, p. 712.

*Primary Examiner*—Max Hindenburg
*Attorney, Agent, or Firm*—Gale H. Thorne

[57] ABSTRACT

A novel two part lancing device comprising a multiple compartment housing for lancets and a carrier. The compartments are joined in a common multiple lancet housing for improved handling and distribution. The housing consists of two end compartments and at least two serially linked, frangibly separable, disposable lancet compartments which comprise presterilized, self-actuating lancets. When fired, each lancet, driven by a precocked torsion spring, executes one reciprocal cycle wherein the lancet tip is driven outward a precise distance to lance a patients finger or the like and is then fully retracted into the housing compartment. The spent lancet can be frangibly separated from the housing to provide access to the next-to-be-used lancet which remains aseptically pure until the moment of separation of the spent lancet. Because the used lancet tip is fully retracted into the housing, the separated lancet compartment can be safely discarded without special handling. The carrier is a handler for the lancet housing and provides a convenient tool of constant length and "feel" for positioning and firing the lancets.

36 Claims, 10 Drawing Sheets

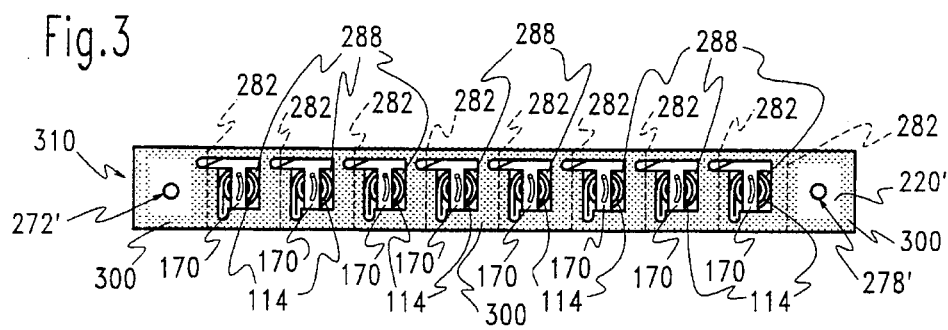
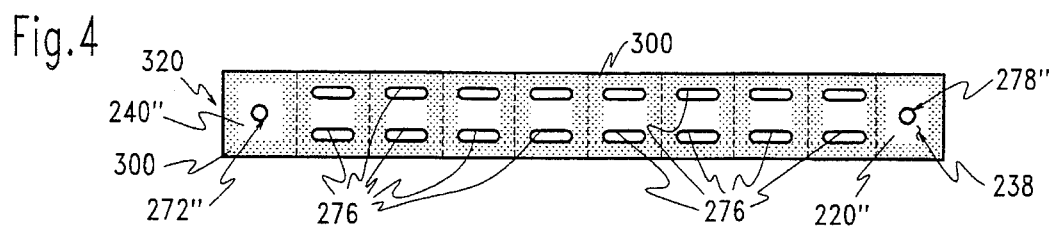
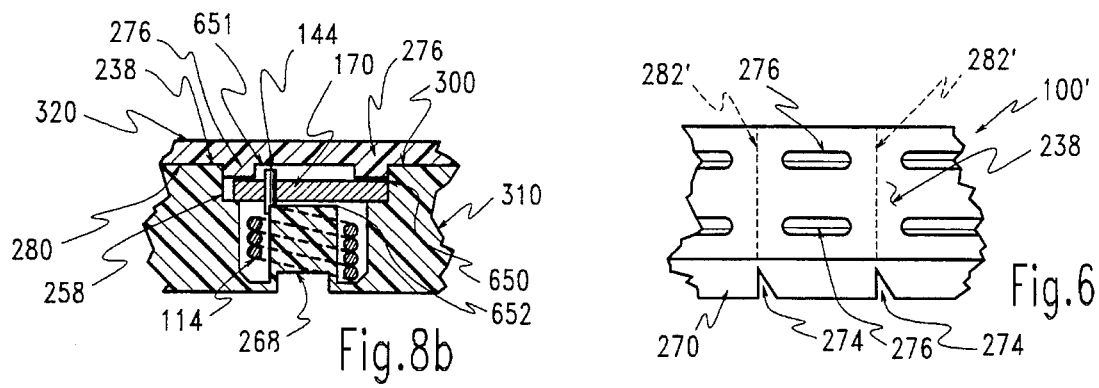
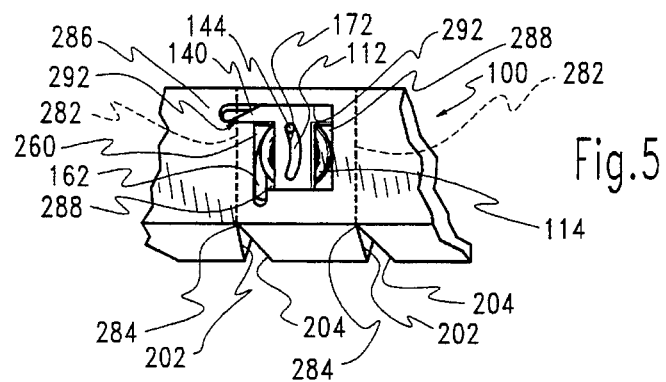

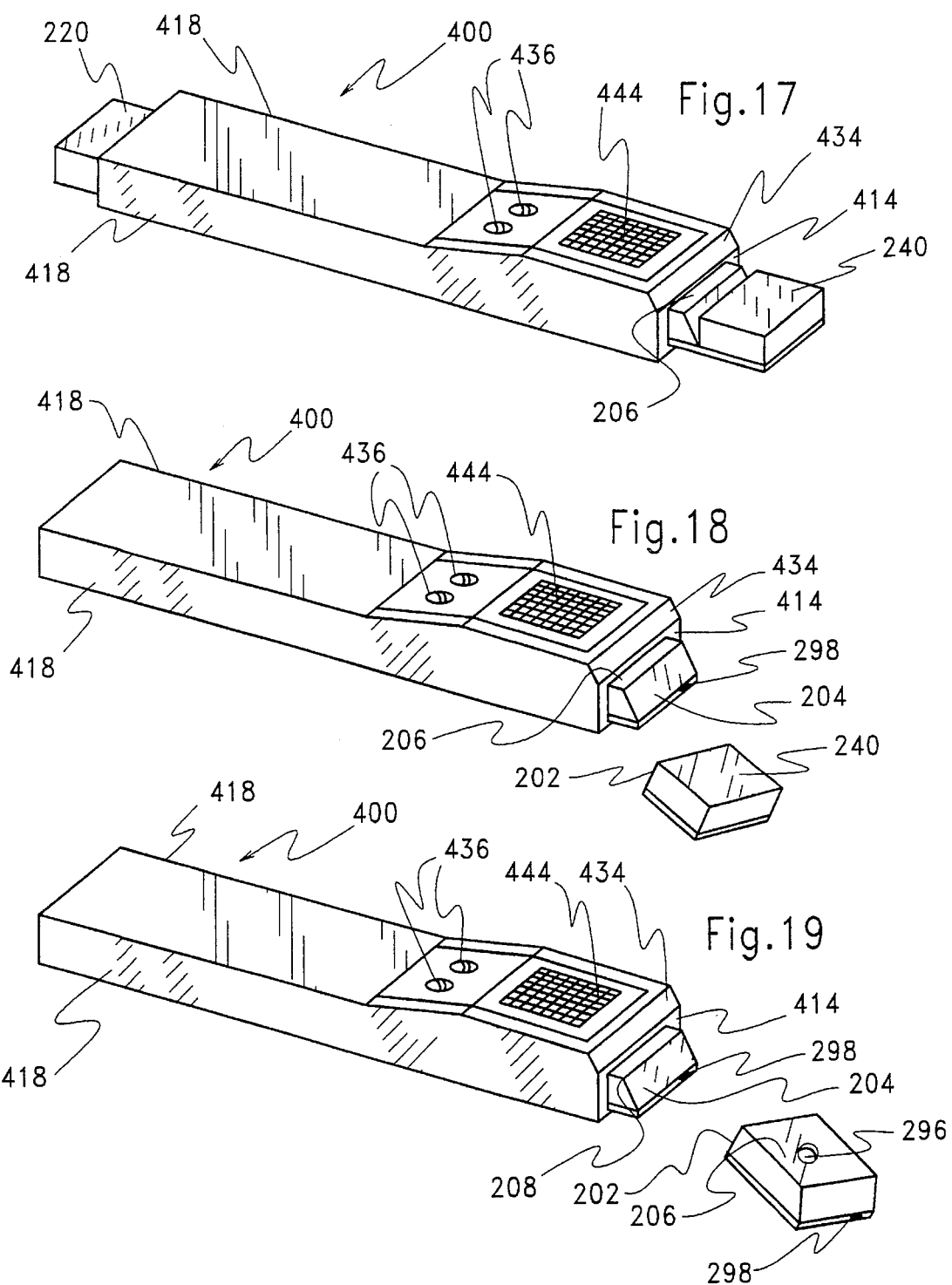

MULTIPLE SEGMENT ENCAPSULATED MEDICAL LANCING DEVICE

FIELD OF INVENTION

This invention relates generally to lancets and more particularly to a novel medical finger-pricking or lancing apparatus, and related methods, the preferred apparatus comprising a hand held carrier, a self-actuating disposable lancet and a housing encapsulating the lancet both before and after use. Multiple disposable lancets in series are packaged together in common for improved handling and distribution. Each disposable encapsulated lancet comprises its own precocked actuator which, when released, fires a lancet tip outward beyond the encapsulating housing into the finger of a medical patient and then safely retracts the spent lancet tip back into the encapsulating housing. The housing is preferably sealed to maintain the sterility of each lancet until opened for use. That portion of the housing which encapsulates each lancet is preferably frangible such that each separate lancet segment may be manually broken off and discarded after use. The hand held carrier receives the interconnected series of encapsulated lancet segments and is used to correctly position and fire each lancet.

PRIOR ART

In the United States, over 700 million blood sampling finger pricks are performed annually. The major reason for the large volume of finger pricks in the United States and abroad is glucose testing, which accounts for over 600 million finger pricks each year in the United States. Other testing processes which utilize finger prick testing comprise blood bank presample testing and blood tests which comprise capillary size samples on the order of 100 microliters or less.

In the past, finger lancing has been performed by medical technicians using hand held fully exposed lances. More recently, with the increased rate of glucose self-testing by patients who have diabetes, finger lancing using hand held fully exposed lances has been replaced by the use of automated lances which employ disposable lancets. Such automated lances are usually superior to hand held exposed lances for reasons comprising better control of puncture depth, lancet velocity, and position. In addition, the act which triggers lancing is remote from the site to be lanced and the lancet including the tip thereof can be hidden from view of patient, factors which are important in self-lancing.

Disposable lancets of the prior art may vary slightly in size and style. Such prior art disposable lancets are commonly formed by injection molding a metal lancet shaft, comprising a very sharp tip, into a totally enclosed plastic housing which provides a protective cover, maintains lancet sterility and makes the unused disposable lancet safe for handling and insertion into an automated lance.

To use the disposable lancet, a header is removed from the automated lance revealing an insertable connection into which the base of the disposable lancet can be introduced. The disposable lancet base is on the end of the disposable lancet opposite the lancet tip. Introduction of the disposable lancet usually involves pushing the lancet base at the time of use far enough into the automated lance to compress a spring which for the first time cocks a firing apparatus of the automated lance. The above described disposable lancet introduction and cocking can be performed safely because the lancet tip is covered by the plastic enclosure. However, once the disposable lancet is in place and the automated lance is cocked, one segment of the plastic enclosure is removed exposing a very sharp lancet tip. The user usually retains the removed segment for later use in lancet disposal. The header is replaced and the automated lance is ready to be positioned and fired.

When the automated lance is fired, the lancet tip is discharged outward a predetermined distance through a hole in the header to pierce the targeted tissue and is then fully retracted inside the header. To prepare the automated lance to lance again, the header must be detached and the disposable lancet removed. However, the very sharp lancet tip is now contaminated and presents a serious first risk for medical personnel. The contaminated tip must be handled with great care. Usually the segment of the plastic enclosure earlier removed is carefully threaded over the lancet tip. This creates a second major risk for medical personnel. Only when the tip is covered has the danger to medical personnel been reduced. The second risk is substantial because the hole in the segment is only the diameter of the lancet shaft and the nearly spherical enclosure segment is less than one quarter of an inch in diameter. Thus, if insertion misalignment occurs, the lancet tip can puncture and contaminate the medical attendant. A third risk exists since, through inadvertent use the technician may recock the used lancet and use it again on another patient.

Self-contained disposable lancets which require no other lances, housings, or carriers and automatically retract spent lancets to become totally disposable are known, but are complex and their use is severely limited by their high cost relative to automated lance and disposable lancet apparatus due mainly to the complexity of the apparatus used to house, cock, fire, and recover lancets. The Heal Stick Lancet available from Surgicutt Hemochron is expensive and not intended for finger lance usage. Each such prior art lancet is provided in one lancet at any one point in time. Also, the general size of self-contained disposable lancets is relatively large due to inclusion of triggering and firing mechanisms in each lancet package. These, and all other known disposable lancets, are only available in a single lancet format.

U.S. Pat. Nos. 4,627,445 and 4,637,403 as well as the aforesaid Heal Stick typify the above mentioned lancet prior art.

BRIEF SUMMARY AND OBJECTS OF THE INVENTION

In brief summary, this novel invention alleviates known major problems related to providing low cost disposable lancet devices and safe disposal thereof. The invention comprises individually disposable encapsulated lancets packaged in a multiple lancet housing and a carrier which comprises a handler for the housing and a trigger to fire the lancets and related methods.

The actuator for each disposable lancet device comprises a spring biased against its memory prior to encapsulation. In some presently preferred embodiments of the invention, one end of a torsion spring comprises a piercing element shaft and tip such that the disposable piercing element and the spring are formed as one piece. In other presently preferred embodiments, the lancet device comprises multiple parts such as a torsion spring coupled to a preformed and sharpened piercing element. Through novel translation of angular motion of the spring to linear motion of the lancet, two way displacement of each piercing element occurs, i.e. the piercing element is driven outward by release of the force of memory at the spring a predetermined distance to precisely pierce a desired body site and thereafter the piercing element is completely retracted by the spring as it unwinds. The conversion of one form of motion to reciprocal motion of the piercing element may be achieved by novel cam/cam follower structure.

The encapsulating housing comprises serially linked frangible lancet compartments which are preferably presterilized and wherein the sterility of each lancet is maintained until a specific compartment is opened for use. Each compartment (and the associated encapsulated spring and piercing element) is frangibly separable from the remainder of the housing such that used compartments with fully retracted spent lancets can be separated and safely discarded. The housing may be also marked with a series of grooves which match a detent apparatus in the carrier. The detent arrangement causes the housing to be correctly positioned juxtaposed carrier's trigger apparatus, allows, after insertion, only proper unidirectional movement of the housing through the carrier, and firmly restrains the housing from movement during lancing. Thus, the carrier provides a fail safe handler for the housing while providing a tool of constant "feel" when using the housing which shortens with use.

Accordingly, it is a primary object to provide a novel and improved blood droplet lancet device.

It is a principal object to provide a series of disposable self-actuating lancets.

It is a further principal object to provide a carrier for handling and selectively triggering each of a series of disposable lancets.

It is an important object to provide one form of bias motion which is converted into substantially reciprocal linear piercing element outward motion for patient finger or the like penetration and piercing element retraction.

A further dominant object is the utilization of rotary motion of a torsion spring, upon actuation to linearly bidirectionally drive a piercing element.

It is a further important object to provide guides within the housing to control the line of travel of a piercing element of a lancet.

It is a consequential object to provide a disposable manually selectively actuated lancet device which totally retracts the lancet tip into an encapsulating housing at the end of the firing and patient penetration cycle such that the used lancet device can be safely handled and discarded as is, after use.

It is a dominant object to provide a plurality of encapsulated disposable lancets wherein each encapsulated lancet is manually frangibly separable from the other encapsulated lancets such that each used encapsulated lancet is broken off and discarded.

It is an elemental object to provide a segmented housing encapsulated a plurality of lancet structures which permits each lancet to be used only once, then severed from the remainder of the housing and discarded.

It is a further significant object to provide manually actuated lancet device and encapsulating housing which precisely controls lancet penetration depth.

It is a further chief object to provide a plurality of disposable lancets encased within housing wherein each lancet comprises selectively releasible bias means.

It is a foremost object to provide a disposable selectively actuated one piece lancet device comprising a single steel spring wire wound as a torsion spring and sharpened to form a lancet tip on one end.

It is a further foremost object to provide a disposable selectively actuated lancet device comprising torsion wound spring formed separately but coupled to a piercing element combined with guide structure which defines the path of the piercing element responsive to release of the spring.

It is a basic object to provide a plurality of disposable manually selectively actuated lancets encapsulated in a housing which comprises individual frangible lancet compartments which are individually sealed such that contamination of the lancet in one compartment through use or otherwise does not contaminate any other compartment.

It is a further paramount object to provide a plurality of disposable selectively actuated lancets encapsulated in a housing which comprises individual frangible lancet compartments which are hermetically sealed and aseptically treated and require no further sheath to insure preservation of long or short term sterility.

It is an object of significance to provide a disposable manually actuated lancet apparatus which can be used alone or as part of a disposable sensor.

It is a fundamental object to provide a carrier or instrument for a disposable lancet housing wherein opposed detent structure is provided to accurately locate the housing within the carrier or instrument so that one or more encapsulated, biased, piercing elements may be selectively actuated.

It is a further fundamental object to provide a lancet housing comprising at least one frangible trigger by which one or more lancets encapsulated in the housing are selectively actuated.

It is a meaningful object to provide a holder, carrier or instrument for a disposable lancet housing which physically limits housing orientation therein and direction of travel such that an insertion error cannot be made.

It is a key object to provide a holder, carrier or instrument for a disposable lancet housing which firmly substantially prevents housing movement within the carrier during lancing.

These and other objects and features of the present invention will be apparent from the detailed description taken with reference to accompanying drawings.

BRIEF DESCRIPTION OF THE DRAWINGS

FIG. 3 is a planar view of the inner surface of the lancet housing assembly member with torsion spring and lancet blade in place and adhesive distributed on the higher surfaces;

FIG. 4 is a planar view of the inner surface of the lancet cover housing member with adhesive distributed on the higher surfaces which contact juxtaposed surfaces of the lancet housing assembly member shown in FIG. 3 when rotated and joined to form a lancet housing;

FIG. 5 is a perspective view of a lancet compartment of the housing member shown in FIG. 3;

FIG. 6 is a perspective view of the portion of a lancet cover housing member for the lancet compartment in FIG. 5;

FIG. 8b is a section taken along lines 8b—8b in FIG. 7, shown with lancet and lancet housing cover added to show vertical relationship of housing, lancet, spring, and cover;

FIG. 11a is a section of FIG. 11 along line 11a—11a;

FIG. 11b is a section of FIG. 11 along line 11b—11b;

FIG. 13 is a section along lines 13—13 of FIG. 12a;

FIG. 17 is a perspective drawing showing initial position of a new lancet housing properly inserted into a housing carrier;

FIG. 18 is a perspective drawing showing the distal end of a new lancet housing frangibly separated from the housing revealing the exit aperture for the first to-be-used lancet; and FIG. 19 is a perspective drawing showing a used lancet compartment frangibly separated from the remainder of the housing revealing the exit aperture for the next to-be-used lancet.

DETAILED DESCRIPTION OF THE ILLUSTRATED EMBODIMENTS

In this description, the term proximal is used to indicate the segment of the device normally closest to the operator when it is being used. The term distal refers to the other end. Reference is now made to the embodiments illustrated in FIGS. 1–19 wherein like numerals are used to designate like parts throughout.

Figure 1:
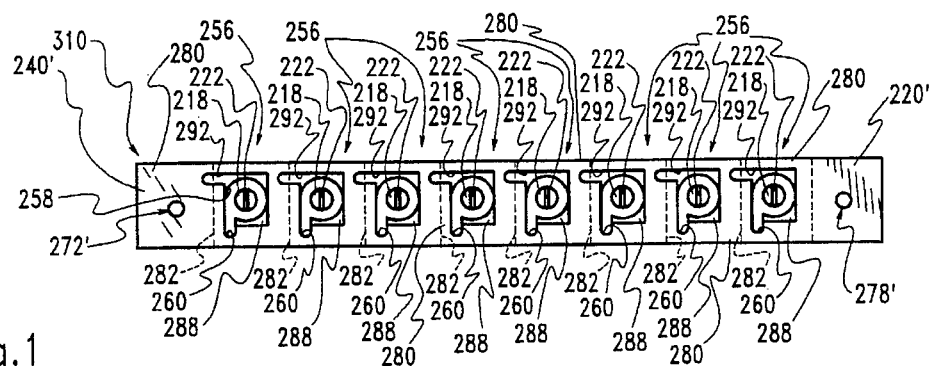
FIG. 1 is a planar view showing the inner surface of the lancet housing assembly member.

Reference is made to FIGS. 1 which shows the inner surface of the lancet assembly member 310 of the currently preferred embodiment of the lancet enveloping and encapsulating housing. Assembly member 310 comprises distal end 240', proximal end 220', and multiple empty housing compartments 256 separated by frangible segments 282 where the housing compartments can be separated. Assembly alignment pin holes 272' and 278' are also shown. Construction of each housing compartment 256 is substantially the same as each of the others. As can be more easily seen in FIG. 1A, typical housing compartment 256 comprises a hub 218, torsion spring anchor slot 260, lancet slide plane 288, guides 292, and frangible section 284. Hub 218, placed substantially in the center of compartment 256, is part of the lancet triggering mechanism which will be discussed in detail later. A groove 222 across the centerline of hub 218 provides a locking apparatus for that part of a torsion spring which will drive the lancet when the spring is freed to unwind. Torsion spring locking slot 260 holds the lower end of the torsion spring immobile in compartment 256. Lancet slide plane 288 is inset below inner surface 280 to provide lancet edge guides 292 parallel to the line of travel on each side of a lancet. The lancet slide plane 288, edge guides 292, and travel limit edge 258 (to be described in detail later), an integral part of the lancet structure and function, are included in the encapsulating housing structure in this embodiment.

Channel 286 which is an extension of slide plane 288 extends across frangible area 282 such that, when a top cover completes the housing and separation occurs at frangible section 284, egress/ingress port or aperture 298 is opened. The line of separation is determined by the "V" groove having an apex at section 284 and formed by compartment end apparatus comprising vertical end 202 and slanted end 204. Function of the frangible section and end apparatus is discussed in more detail later.

Figure 1A:
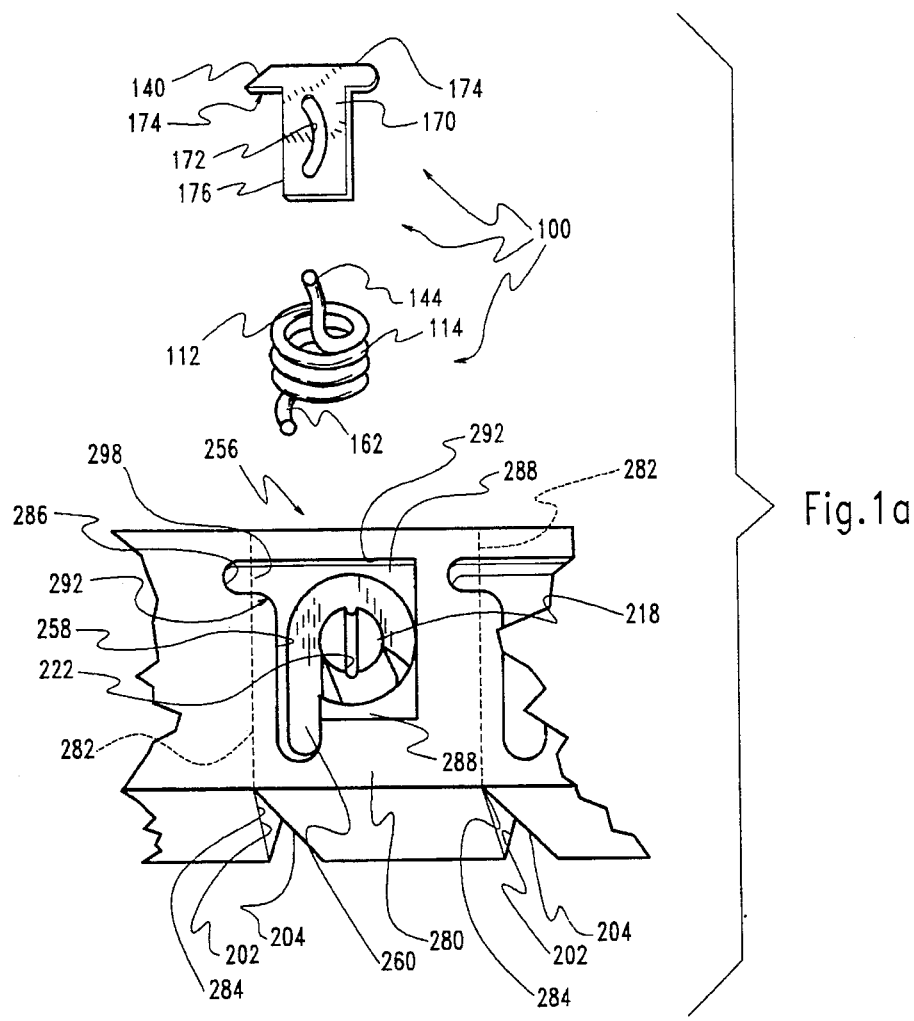
FIG. 1a is an exploded perspective view of a lancet housing assembly compartment comprising a lancet blade and torsion spring in cocked orientation.

Other than spring release associated with hub 218, the moving parts of the lancet comprise torsion spring 114 and lancet blade 170. A currently preferred embodiment of torsion spring 114 is shown in FIG. 1A. The spring comprises spring wire wound into a torsion spring having a lower end 162 which extends horizontally outward from spring 114. On the other end, the spring is bent centrally such that it forms a straight horizontal segment 112 which can be locked into groove 222 when wound torsion spring 114 is press-fit over hub 218. To assemble the lancet, tightly wound torsion spring 114 is pressed over hub 218 such that lower spring end 162 is firmly affixed into anchor slot 260 and horizontal straight spring section 112 is firmly pressed into groove 222. At the wire end of straight segment 112 the spring is bent vertically upward forming crank arm 144 which comprises the interlocking between torsion spring 114 and coupling slot 172 of lancet 170. Thus, crank arm 144 comprises a cam and arcuate coupling slot 172 comprising a cam follower, the cam/cam follower structure, sometimes referred to as track structure, provides rotary to linear motion translation.

In one currently preferred embodiment, lancet comprises lancet blade 170 which is of unitary, stainless steel construction comprising a very sharp lancet tip 140, torsion spring 114 coupling slot 172, guide edges 174, and leading edge 176. To complete assembly of lancet bottom housing 100 in compartment 256, lancet slot 172 is placed over already positioned torsion spring crank arm 144 such that lancet blade 170 lies on slide plane 288 with lancet tip 140 in channel 286 and edges 174 in line with edge guides 292.

Figure 7A:
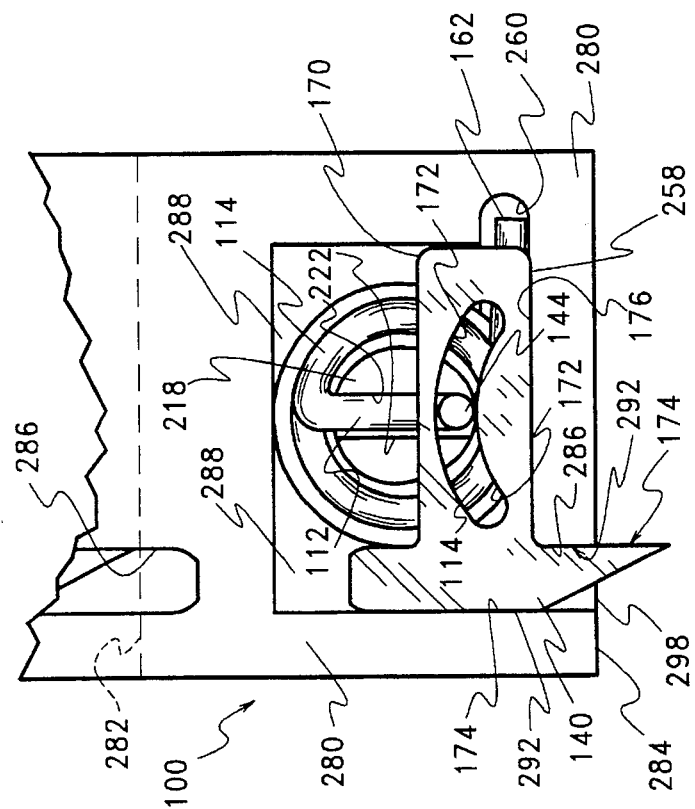
FIG. 7a is a top elevation of a lancet compartment FIG. 7 showing fired lancet in mid-cycle wherein the lancet tip is protruding from the lancet compartment.
Figure 7:
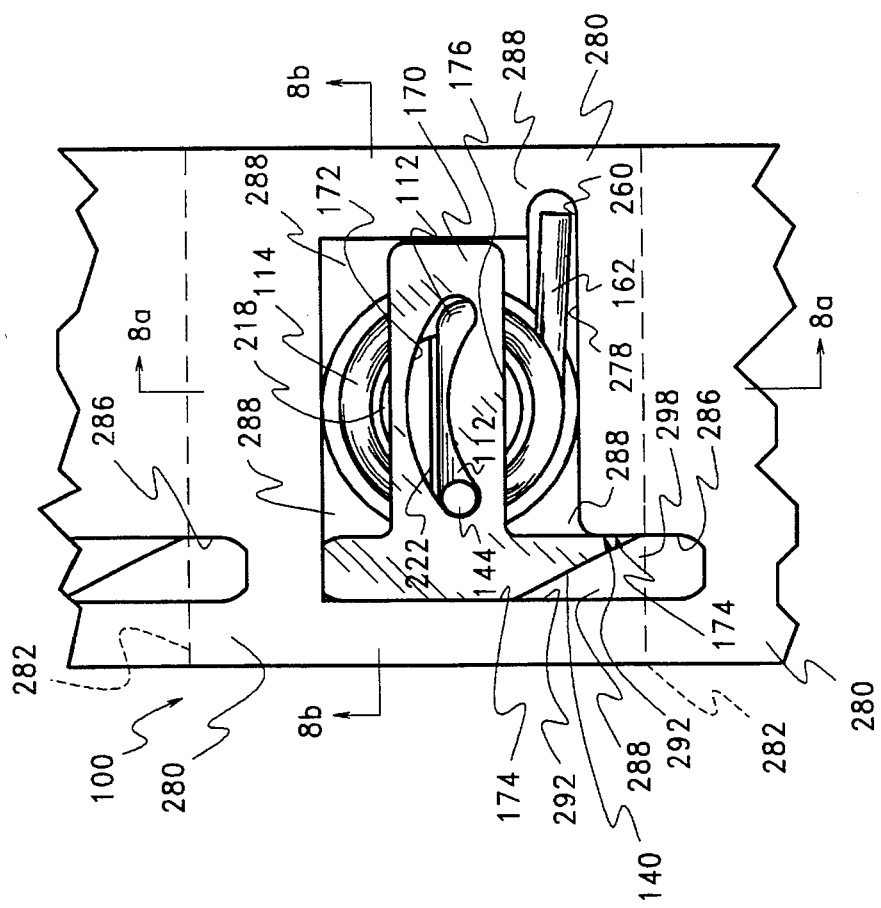
FIG. 7 is a top elevation of an assembled lancet compartment of the currently preferred embodiment of the invention with lancet cover housing removed.

A planar view of assembled lancet bottom housing 100 is shown in FIG. 7. The housing cover, which normally covers lancet bottom housing 100 is not shown for clarity of presentation. Torsion spring 114 is cocked and held firmly in place by slot 260 and groove 222. Before the lancet can be fired, lancet tip 140 exit aperture 298 is opened by frangibly separating lancet bottom housing 100 along frangible area 282.

Figure 8A:
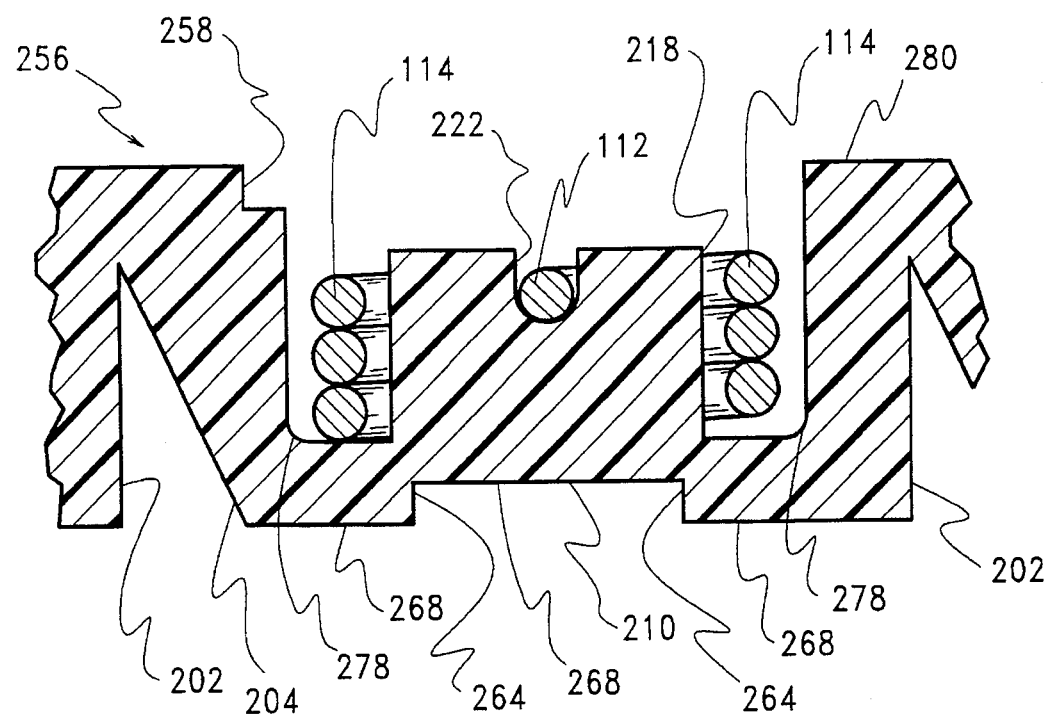
FIG. 8a is a section taken along lines 8a—8a in FIG. 7; shown without lancet for clarity of presentation.

The lancet is actuated by breaking attachment of hub 218 free from compartment 256. One mode of actuation is best seen in FIG. 8a which is a section along lines 8a—8a of FIG. 7. Hub 218 is connected to compartment 256 by frangible diaphragm 268 comprising rounding corners 278 and sharp corners 264. Frangible diaphragm 268 comprises an actuator which first holds hub 218 from movement and, upon actuation, releases hub 218 to rotate as forced by the released biasing memory of torsion spring 114. Recess 210 causes actuator diaphragm 268 to be attached to hub 218 with a reduced cross section at sharp corners 264 forming an actuator. To actuate the lancet, an external force is applied to recess 210, causing actuator diaphragm 268 and hub 218 to be deflected slightly. This deflection causes stresses to be generated at sharp corners 264 and results in fracture of hub 218 from actuator diaphragm 268 at sharp corners 264. When viewed from the inner surface 280, freed hub 218 is released by the actuator to spin in a counter clockwise direction as the biasing memory of the cocked torsion spring 114 is freed to unwind.

Figure 7B:
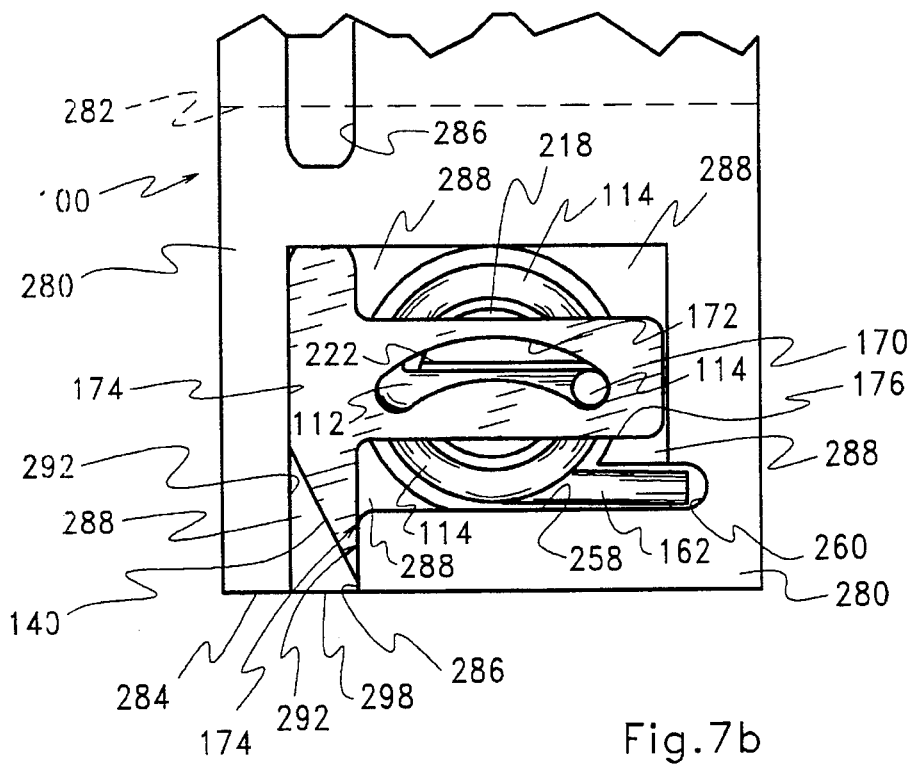
FIG. 7b is similar to FIG. 7 showing a spent lancet with the lancet tip retracted into the lancet compartment.

As can best be seen in the sequence of FIGS. 7, 7A, and 7B, as hub 218 and spring 114 rotate, crank arm 144 moves in nearly circular motion, sliding laterally in slot 172 as it drives the lancet tip 140 linearly outward through the egress/ingress port 298 from the face of frangibly separated section 284. As shown in FIG. 7A, lancet blade 170, guided by edges 292 and forced by crank arm 144, moves lancet tip 140 outward until leading edge 176 of lancet blade 170 collides with travel limit edge 258. In this manner, the depth of lancet tip 140 penetration is precisely determined. The depth of puncture in the currently preferred embodiment is 1.7 to 3.0 millimeters.

The further unwinding of torsion spring 114 continues to drive crank arm 144 in a nearly circular counter clockwise direction causing lancet blade 170 to be retracted as shown in FIG. 7B, completing translation of torsion spring 114 rotary motion to bidirectional linear travel of lancet blade 170. With a cover in place, lancet compartment 256, now containing a totally retracted spent lancet 170 is a safe disposable. There is no "bounce" or multiple excursion of lancet tip 140 from the housing because the forcing direction of the biasing memory of the torsion spring forces lancet 140 away from travel limit edge 258 and egress/ingress port 298.

Figure 2:
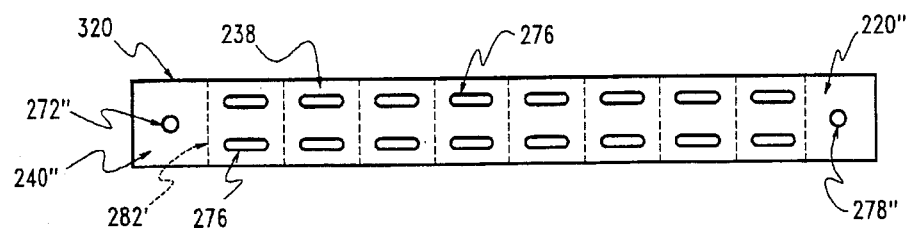
FIG. 2 is a planar view of the inner surface of the lancet cover housing member.

Enveloping or encapsulating housing cover 320 is shown in FIG. 2. End sections 240" and 220" are patterned to be juxtaposed over assembly member 310 distal and proximal ends 240' and 220' with assembly alignment pins 272" and 278" inserted into assembly alignment pinholes 272' and 278', respectively.

Raised lancet blade 276, shown in FIGS. 2, 4, and 6 are located to fit within compartment 256 during assembly. As is seen in FIG. 8b, blade guides 276 position lancet blade 170 away from bonding surfaces 280 and 238, thus preventing inadvertent blade adhesion or immobilization during assembly. Also, blade guides 276 establish lancet blade vertical clearance 650 and drive crank arm clearance 651. Lancet blade vertical clearance 650 is set at approximately 0.005 inches and allows for free translation of blade 170. Drive crank arm clearance 651 must be large enough to prevent drive crank arm 144 from rubbing on cover 320 when hub 218 is fractured and displaced towards cover 320 during firing. Drive crank arm clearance 651 is set in conjunction with lancet blade vertical clearance 650 and hub to blade clearance 652 so as to maintain positive clearance between 144 and 320 during operation.

Figure 14:
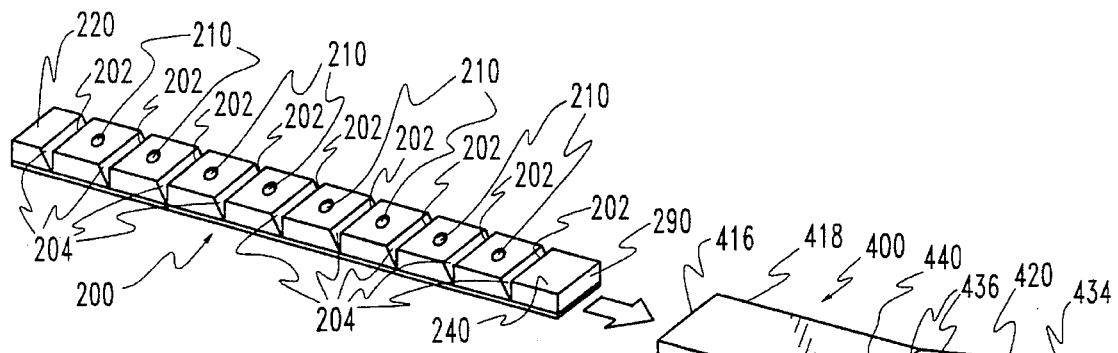
FIG. 14 is a perspective drawing showing direction of insertion of a lancet housing into a housing carrier.

After lancet device assembly, the inner surfaces of assembly member 310 and cover member 320 are bonded together to form hermetically sealed lancet housing 200, as shown in FIG. 14. Both members can be molded from synthetic resinous material such as, but not limited to, polymethylmethacrylate, filled polypropylene, polystyrene, and acrylics. Depending upon material used, bonding can be accomplished by using methods comprising adhesives and thermal and ultrasound heating processes.

Polymethylmethacrylate is the material of choice in the currently preferred embodiment of the enveloping or encapsulating housing. Polymethylmethacrylate is moldable, currently inexpensive, strong and may be glued or ultrasonically bonded. Also polymethylmethacrylate undergoes little elongation prior to fracture, resulting a minimum of part distortion when frangible parts are broken.

Adhesive 300 is applied to one or both planar surfaces 280 and 238 as shown in FIGS. 3 and 4 and the two members are compressed and bonded together to complete the lancet housing 200 otherwise known as a lancet packet. As shown in FIG. 6, serrated grooves 274 are formed such that, when housing cover 100' is bonded to lancet bottom housing assembly 100 to form lancet housing 200, frangible area 282 of lancet bottom housing 100 is juxtaposed with housing cover 100' frangible area 282' completing frangible section 284. Lancet housing, so formed, provides a hermetically sealed encapsulation for the lancets therein contained.

In this first described embodiment, the elements of the lancet comprise the following: (a) finger pricking or finger piercing elements comprising lancet blade 170 comprising lancet tip 140 and slot 186: (b) biasing memory elements which comprises the potential energy source by which the lancet is actuated and which comprise torsion springs 114 tightly wound and stored in precocked condition to be released by an actuator: (c) motion displacement control and transforming elements comprising edge guides 292, travel limit edge 258, and motion or displacement control or conversion elements which comprise slots 186 which transform the rotary motion of a released torsion spring 114 to reciprocal linear motion of lancet tip 140: and (d) actuator elements comprising hub 218 and frangible diaphragm 268 which can be triggerably released to cause the lancet to actuate.

Either prior to or after encapsulation, all internal parts of the packets comprising lancet housing 200 comprising recocked lancets can be sterilized making finger piercing elements aseptic by radioactive, gas sterilization, or like methods which are well known in the art. Each lancet compartment is separately and hermetically sealed from all others such that contamination of the parts of one compartment does not contaminate parts of any other such that each encapsulated compartment is its own hermetically sealed container, retaining an aseptic condition until egress/ingress port 298 is opened.

Figure 9:
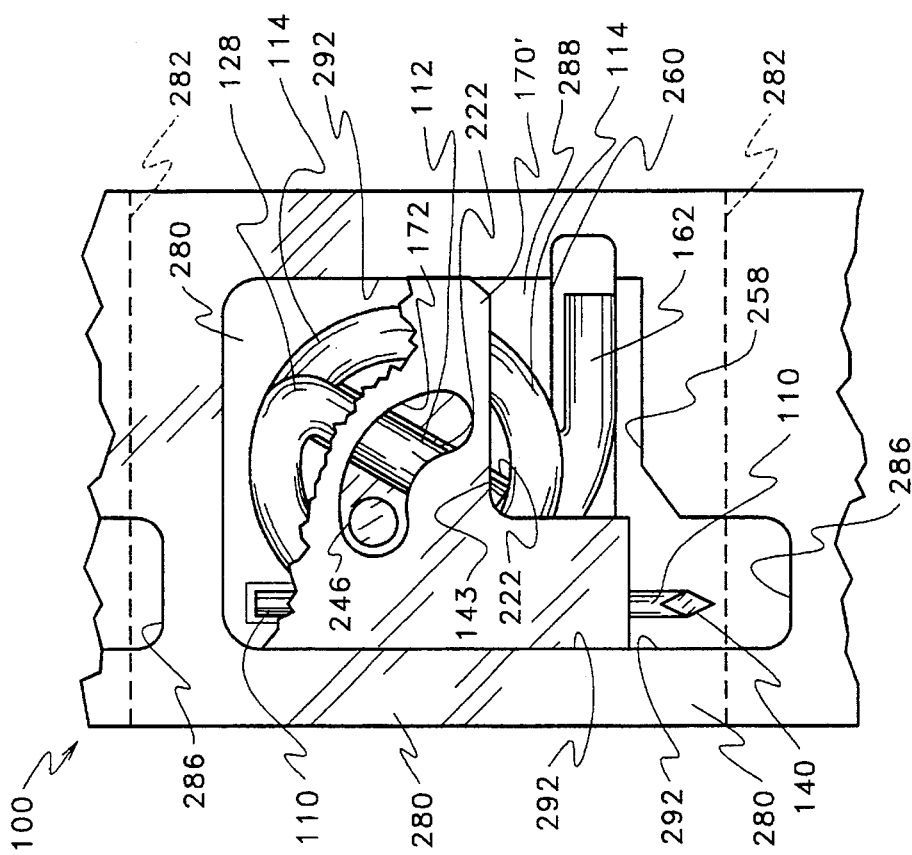
FIG. 9 is a detailed drawing similar to FIG. 7 showing a different embodiment of the lancet and a different coupling to the hub apparatus.

A different embodiment of a lancet with a crank arm apparatus is shown in FIG. 9. In this different embodiment, crank arm 246 is molded directly onto hub 218 to form a cam, allowing a torsion spring 114 to be made without a vertically rising crank arm. Crank arm 246 is of larger diameter than crank arm 144 due to material differences. Larger diameter crank arm 246 also changes the width and geometry of slot 172 which forms the cam follower.

Also as shown in FIG. 9, this different embodiment presents an alternative to stainless steel lancet blade 170 comprising a lancet formed by molding a stainless steel shaft 110, which comprises lancet tip 140, into a synthetic resinous material body to form plastic lancet body 170'.

Figure 10:
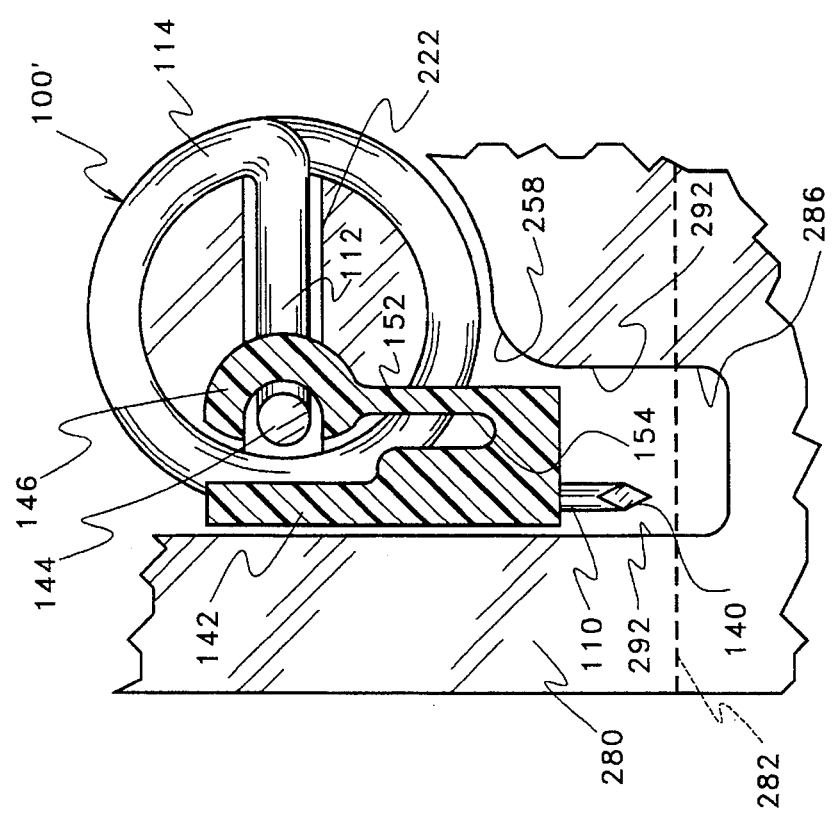
FIG. 10 is planar view of a lancet connected to a torsion spring by a slider crank embodiment.

A further embodiment implements a lancet device comprising slider crank 146 as shown in FIG. 10. In this further embodiment, the lancet shaft 110 is also molded into a synthetic resinous material body. However, in this case said material must be flexible such that when a cam, comprising crank arm 144, rotates in a counter clockwise direction, imposing force of travel against slider crank arm 146, segment 152 of slider crank arm 146 will bend in the area of strain relief 154 allowing travel of lancet tip 140 to be linear as crank arm 146 travels in a nearly circular path. When the linear component of travel parallel to edge guides 292 is outward lancet tip 140 is driven outward. When said linear component of crank arm travel is inward, lancet tip 140 is retracted, ultimately to a safe, fully retracted position.

In this further embodiment, the elements of the lancet comprise the following: (a) finger pricking or finger piercing element comprising slider crank 146, lancet shaft 110, and lancet tip 140; (b) biasing memory element which comprises a torsion spring, tightly wound and stored in precocked condition to be released by an actuator; (c) motion displacement control and transforming elements comprising edge guides 292, travel limit edge 258, and motion or displacement control or conversion elements which comprise crank arm 144 and slider crank 146; (d) actuation elements which can triggerably cause the lancet to actuate.

Figure 11:
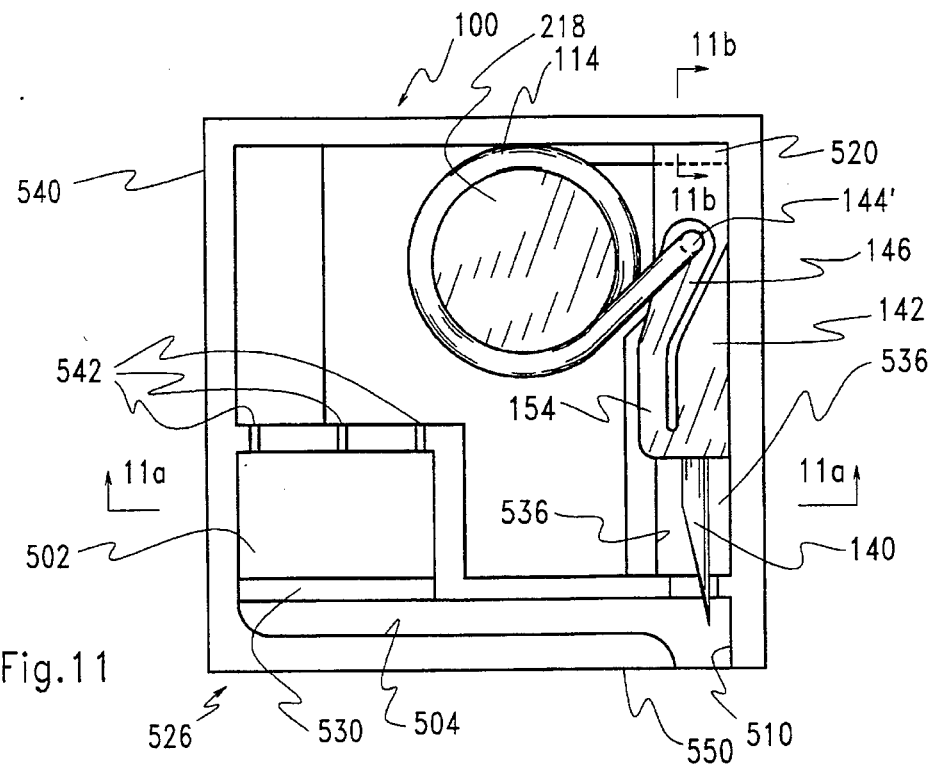
FIG. 11 is a planar view of a lancet assembly in a sensor compartment.

The lancet apparatus can also be used in combination with a chemical assay sensor as shown in FIG. 11. In this sensor embodiment, torsion spring 114 and lancet body 142 share space in housing assembly 526 comprising disposable compartment 540 with sensor pads 502. Lancet body 142 comprises a form similar to slider crank arm 146 (See FIG. 10) and strain relief 154. Crank arm 144' is turned 180 degrees relative to slider crank arm 146 to enter lancet body 142 in a direction away from the inner surface of housing assembly 526.

Figures 11A, 11B:
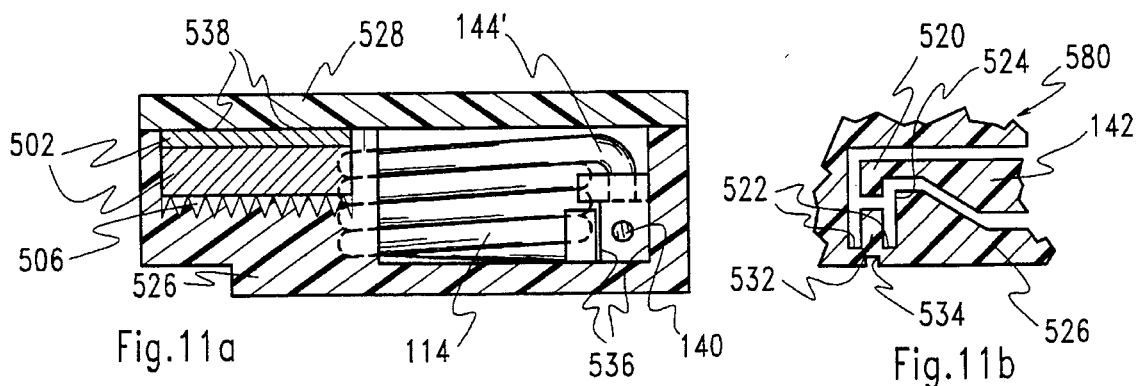

Torsion spring 114 is restrained from unwinding by a slider restraint 580 as shown in FIG. 11B. In this embodiment, latching lancet body 142 comprises latching apparatus 520 at a end distal from lancet tip 140. Latching apparatus 520 is restrainingly hooked against protruding housing assembly member 524. Firing pin 532 is juxtaposed between latching apparatus 520 and housing assembly diaphragm 534. Frangibly breaking thin diaphragm edge connections 522 causes firing pin 532 to be forced against latching apparatus 520, releasibly lifting latching apparatus 520 free from protruding housing assembly member 524 to fire the lancet.

Figure 11C:
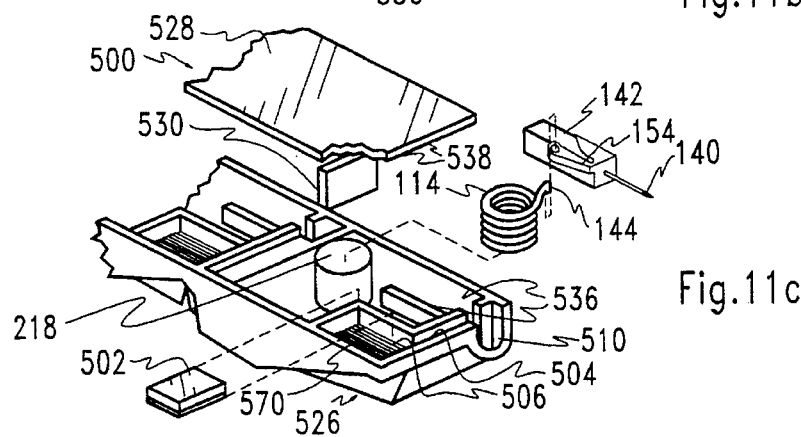
FIG. 11c is an exploded perspective of a sensor compartment showing lancet and sensor component parts placement into a sensor compartment.

The presently preferred procedure for assembling a lancet into sensor compartment 540 can be best visualized by viewing FIG. 11C. Sensor housing assembly 526 and sensor housing cover 528 are formed of synthetic resinous material which allows sensor compartments 540 to be frangibly, cleanly separated along predetermined lines as described earlier. Each sensor housing assembly 526 compartment comprises a hub 218, sensor component cell 570, capillary intake channel 504, common lancet and sample fluid aperture 510, and lancet guide 536. At the bottom of sensor component cell 570 is a hydrophilic serrated surface 506 which abets sample flow across the inner surface of sensor pads 502. Sample flow is further steered by air release grooves 542 as shown in FIG. 11. The sawtooth form of serrated surface 506 is best seen in FIG. 11A which is a section taken along line 11A—11A of FIG. 11. Sensor electrodes 538 which appear as printed circuit patterns on housing cover 528 are juxtaposed above sensor pads 502.

As can best be seen in FIG. 11, sample is drawn inwardly through common aperture 510 along hydrophillically treated surface of capillary intake channel 504 to sensor component cell 570 where it wets sensor pads 502 to initiate a chemical assay. An implement for maintaining separation of sensor pads 502 from sample fluid in capillary intake channel 504 is provided by flow control member 530 which extends orthogonally inward from housing cover 528. Flow control member 530 can be seen in FIG. 11C where it is revealed by removal of the corner of housing cover 528. When flow control member 530 is inserted into position in sensor housing assembly 526, said flow control member 530 sealingly resides between sensor pads 502 and capillary intake channel 504 to steer flow to the bottom surface of sensor pads 502.

Crank arm 144' is inserted into the aperture in slider crank arm 146. Torsion spring 114 is tightly wound and pressed over hub 218 at the same time lancet body is nested between lancet guide 536 and firmly latched against protruding housing assembly 524.

Figure 12A:
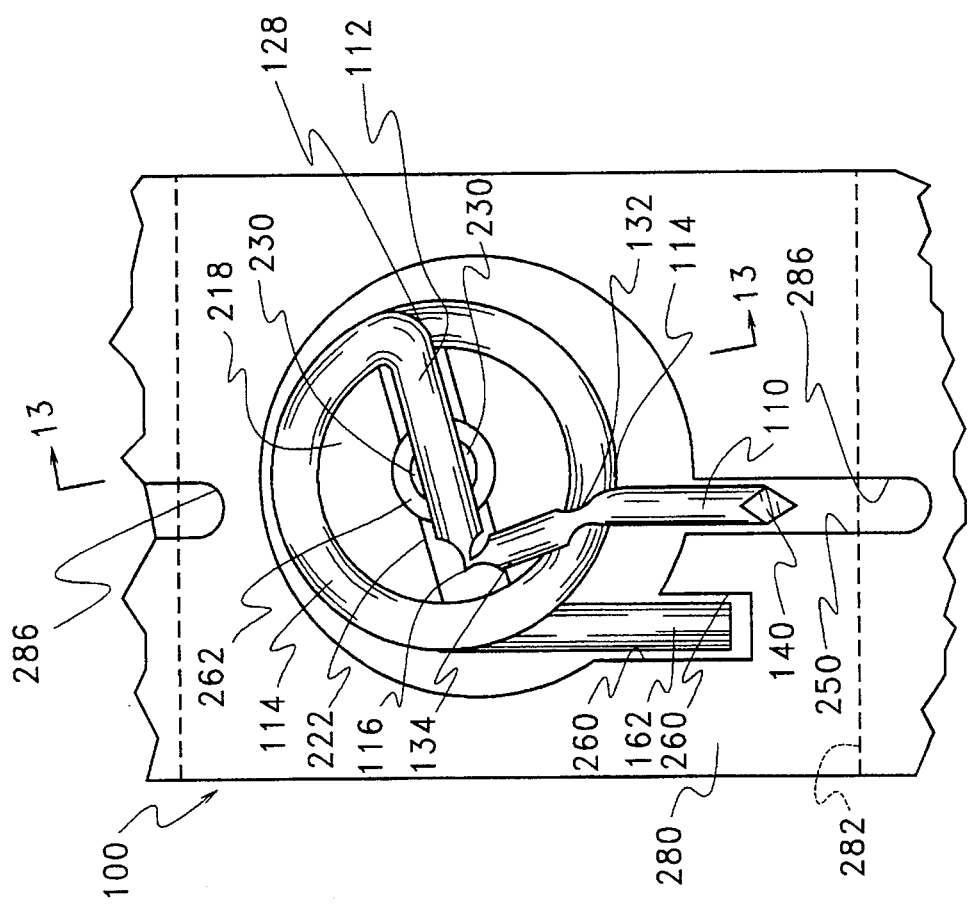
FIG. 12a is a planar view of a lancet fabricated from the one spring wire.

In another preferred embodiment as shown in FIG. 12A, the torsion spring, lancet shaft, and lancet tip are formed from a single length of spring wire. As before, lower spring end 162 is formed to be horizontally held in slot 260. From that end, the torsion spring is cylindrically wound and then formed to angle medially at bend 128 where straight segment 112 extends across torsion spring 114 horizontally and medially such that it can be pressed into groove 222 as heretofore explained. Rather than a crank arm extending upward or downward from the end of segment 112, as described before, the spring wire is there formed into thin hinge member 116. Extending toward the lancet end from thin hinge member 116 is central segment 134 which terminates at second thin hinge member 132. From thin hinge member 132, lancet shaft 110 extends to be wedged into guide groove 250 and terminates at lancet tip 140. In this embodiment, 300 series, austenitic stainless steel spring wire is used. Thin hinge members are ground to nearly rectangular cross sections (i.e. 0.025 diameter wire is ground to 0.025 inch×0.010 inch sections). After grinding, thin hinge members 116 and 132 are heated to incandescence, then cooled, thus forming "living hinges" in the annealed portions of the spring wire.

Figure 13:
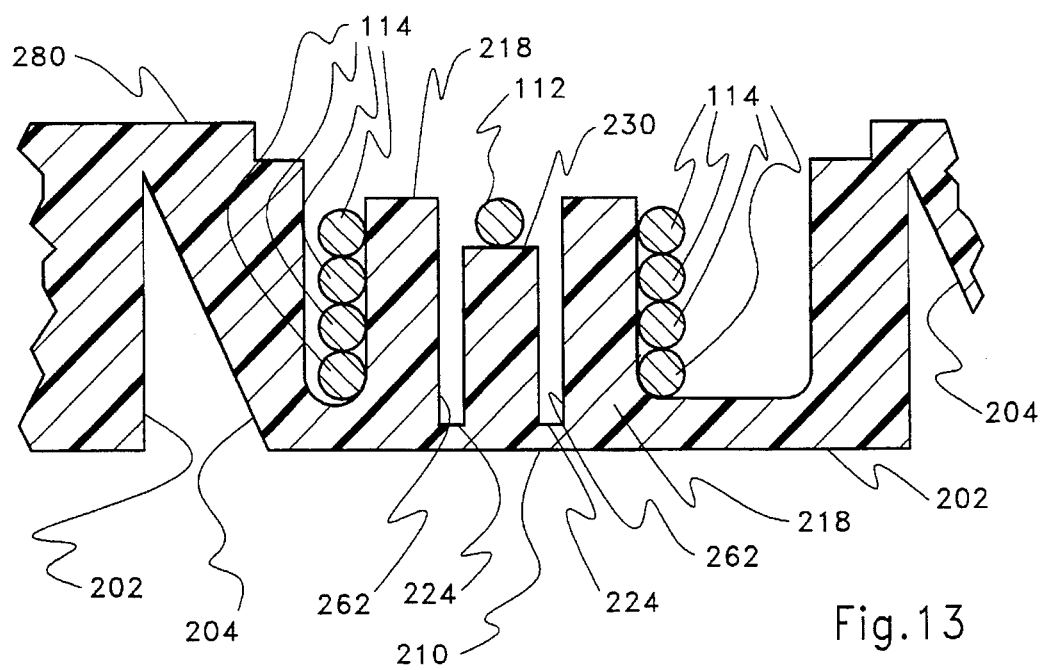

The trigger and release mechanism is also different in this embodiment. FIG. 13 is a cross section along line 13—13 of FIG. 12A and shows the trigger mechanism for this embodiment. Straight segment 112 is shown end on resting on firing pin 230 which rises from hollow cylinder 262 in hub 218. As shown in FIG. 12A, hollow cylinder 262 and firing pin 230 lie juxtaposed with straight segment 112 in the line of groove 222. Though other implements may be used to provide firing pin 230, in this embodiment, firing pin 230 is molded as part of assembly member 310 and is connected to the rest of assembly member 310 by diaphragm 210 comprising thin diaphragm member 224. To fire the lancet, an external force is applied to diaphragm 210 to frangibly sever thin diaphragm member 224 and, to push against firing pin 230 and therethrough against straight segment 112 held in place by groove 222. When sufficient force is applied to break diaphragm 210, firing pin 230 is displaced inward and straight segment 112 is forced from groove 222, thereby allowing torsion spring 114 to unwind and initiate the lancing cycle. In other embodiments, actuation of the lancet can be accomplished by compressing or otherwise distorting the housing to change the position of hub 218 relative to torsion spring 114 such that straight segment 112 is forced from groove 222.

Figure 12B:
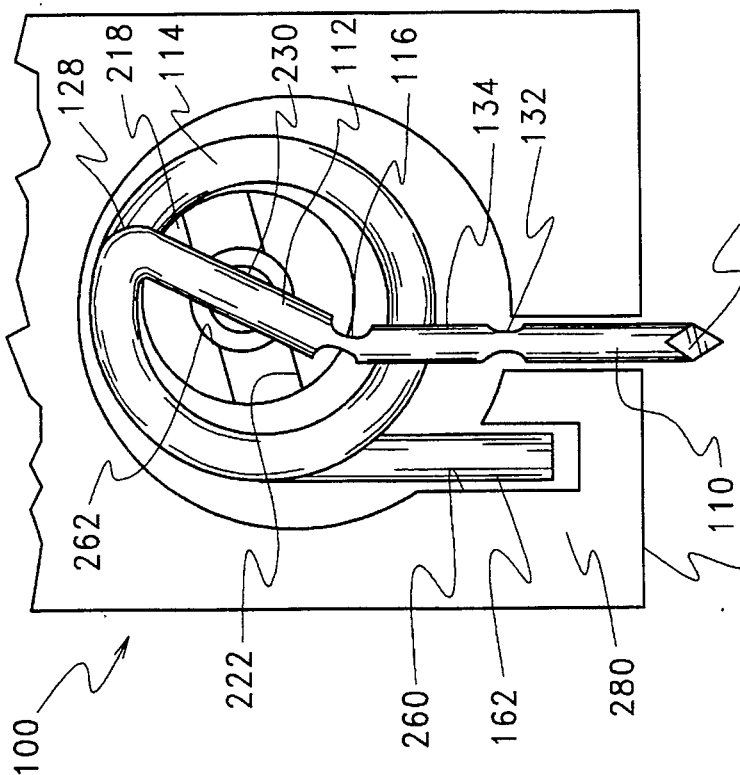
FIG. 12b is a planar view similar to FIG. 12a showing bending of spring wire at the point of greatest outward extension of the lancet tip.
Figure 12C:
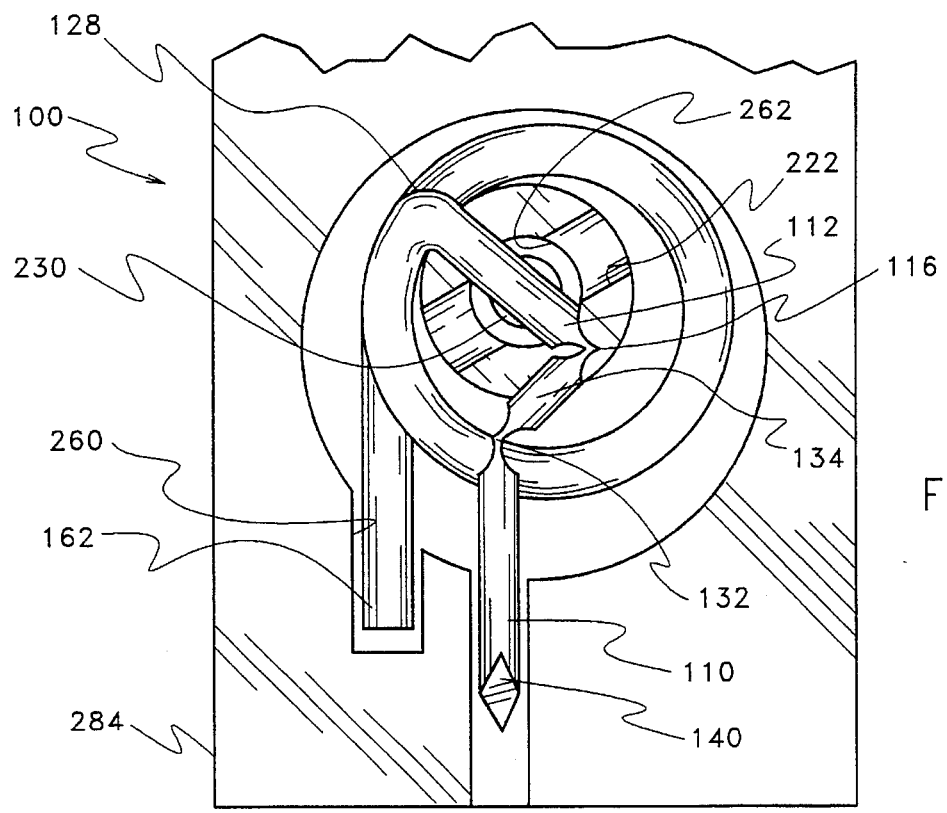
FIG. 12c is a planar view similar to FIGS. 12a and 12b showing continuation of travel of the lancet spring to retract the lancet tip within the lancet compartment.

When torsion spring 114 unwinds, central segment 134 comprising end distortable structure of dual pivot points formed by thin hinge members 116 and 132 bend to force the lancet tip 140 outward through egress/ingress port or aperture 298 from the face of frangible section 284, as shown in FIG. 12B. As torsion spring 114 continues to unwind, thin hinge members 116 and 132 bend to follow the travel of torsion spring 114 and retract lancet shaft 110 and lancet tip 140 into lancet bottom housing 100 as depicted in FIG. 12C.

In this preferred embodiment, the lancet comprises a single element which provides a finger piercing element, a biasing memory, and displacement control or conversion elements and an actuator element comprising firing pin 230 which forces straight segment 112 form groove 222. A motion converting element comprises connected hinge members 116 and 132 at the ends of the distortable structure which comprises central segment 134.

One currently preferred embodiment of the invention comprises a carrier 400 to hold the lancet housing for easier handling as the lancet housing is serially shortened as spent lancets are frangibly separated and discarded. Carrier 400 also provides a special tool for triggering the lancet.

As seen in FIG. 14, lancet housing 200 comprises proximal end 220, eight disposable lancets, and distal end 240. Because carrier 400 is normally held such that carrier end 416 is proximal to the user, housing end 240 is designated the distal end. Before insertion, lancet housing 200 is oriented such that lancet bottom housing 100 is on top, revealing frangible diaphragms 210. To prepare the invention for use, lancet housing 200 is inserted through an aperture in proximal carrier end 416 and slid forward in the carrier tunnel until proximal carrier end 240 exits carrier 400 as shown in FIG. 17. As mentioned earlier, the distal slanted end 204 of each lancet compartment meets with a vertical proximal end of each neighboring lancet compartment to form a "V" groove. The "V" groove is sufficiently deep to form a frangible line for lancet separation and also to act as a catch for a detent. Alignment structures comprise "V" grooves of the housing or packet and matching detents in the carrier tunnel which align and position each packet or housing compartment prior to use.

Instrument or carrier 400 comprises outer shell 418 and an actuator or trigger button 420. Carrier 400 is small enough to be as pocket portable as a felt tipped marker pen and can be fitted with a pocket clip for safe pocket transport. As seen in the exploded view of carrier 400 in FIG. 15, carrier outer shell 418 comprises two parts, carrier bottom 402 and carrier top 422, adhesively bonded together along edges 404 and 412, respectively. Carrier bottom 402 comprises at least two openings 442 which provide access to the lancet housing 200 to slide it into position for each successive firing.

Figure 16:
FIG. 16 is a section of one of the three major parts of the lancet housing carrier along lines 16—16 of FIG. 15.
Figure 15:
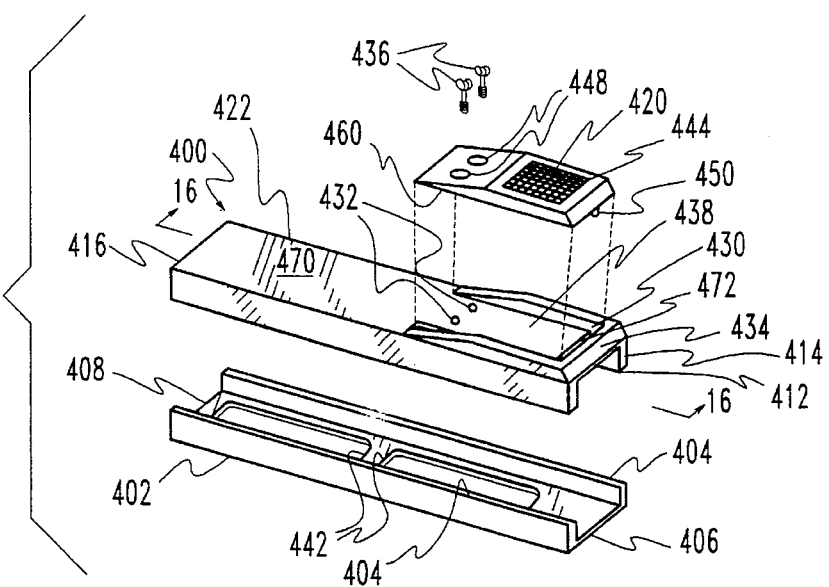
FIG. 15 is an exploded perspective drawing showing the three major parts of the lancet housing carrier.

The carrier top 422 comprises trigger button guard 434, detent tongue 438, trigger slot 430 formed by proximal wall of trigger button guard 434 and distal end of detent tongue 438, and mounting and positioning apparatus for trigger button 420. As seen in FIG. 16, detent tongue 438 comprises "V" shaped detent 472 which compliantly allows passage of lancet housing 200 out of the distal end 414 of carrier 400 and firmly retards movement in the other direction such that the distal end of the lancet housing can be firmly held against the puncture site without slippage of lancet housing 200 back into carrier 400. While detent 472 allows passage of lancet housing 200 through the one way carrier tunnel toward the distal end of carrier 400, it acts as a sensible detent, allowing precise positioning of each diaphragm 210 juxtaposed below trigger apparatus 450 of trigger button 420.

Trigger button 420 comprises trigger apparatus 450, button surface 444, and mounting holes 448. Cylindrical trigger apparatus 450 is of a sufficiently small diameter to fit into the depression which forms diaphragm 210 and is long enough to frangibly break diaphragm 210 and release hub 218 to fire the lancet. Trigger button 420 is attached in cantilevered fashion to the surface 470 of carrier top by two screws 436 which are passed through holes 448 in trigger button 420 and firmly anchored in mounting holes 432.

In use, a packet or lancet housing 200 is inserted into carrier 400 such that detent 472 fits into the "V" groove on the proximal end of first lancet compartment 206. As a result, distal end 240 extends beyond the front edge 414 of carrier 400 as shown in FIG. 17. As shown in FIG. 18, distal end 240 is frangibly separated from the distal end of first lancet compartment 206 revealing lancet egress/ingress port or aperture 298. To perform a finger prick or the like, the lancet egress/ingress port 298 is placed over the site to be pricked and the actuator or trigger button 444 is firmly pressed until lancet tip 140 is discharged. To remove spent lancet 206 for access to the next to-be-used one, the lancet housing is moved distally to the next detent position and spent lancet 206, with disjoined diaphragm 296, is fully clear of carrier 400. Lancet 206 is then frangibly separated as shown in FIG. 19. Because lancet tip 140 is totally retracted into the lancet compartment housing, lancet 206 can be discarded directly. Frangible separation of spent lancet 206 reveals next to-be-used lancet aperture 298 of next available lancet 208 which is ready for immediate use.

The invention may be embodied in other specific forms without departing from the spirit or essential characteristics thereof. The present embodiment are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A disposable lancet actuating apparatus which can be triggered to discharge a lancet tip from a housing and retract the lancet tip into the housing for safe disposal comprising:

a lancet body comprising the lancet tip;

means for storing energy which can be released from a state of high potential energy to provide a unidirectional angular form of kinetic energy through a period of time while energy is being released, said energy storing means comprising means for communicating with a triggerable release;

means for coupling between the energy storing means and the body such that kinetic displacement of the energy storing means forcefully drives the lancet tip linearly outward from the housing and then forcefully retracts the lancet tip back into the housing through the period of energy release;

the housing comprising:
means for enveloping and encapsulating the lancet body;
a manually operated triggerable release for releasing the energy storing means from the high potential energy state thereby permitting the lancet tip to be triggerably actuated;
guide means which restrain travel of the lancet tip to linear motion;
means for precisely limiting depth of lancet tip penetration.

2. A disposable lancet actuating apparatus according to claim 1 further comprising means for frangible attachment to at least one other lancet actuating apparatus.

3. A disposable lancet actuating apparatus according to claim 1 wherein said energy storing means comprise torsion spring means which comprise a first end which is immobilized within the housing.

4. A disposable lancet actuating apparatus according to claim 1 wherein said triggerable release comprises a frangible connection to the rest of the housing.

5. A disposable lancet actuating apparatus according to claim 1 wherein the housing comprises means for restricting the linear motion to one reciprocal cycle, thereby restricting said lancet actuating apparatus to being used just once and lancet tip entry into a patient but once.

6. A disposable lancet actuating apparatus according to claim 1 wherein the housing comprises actuating means which are irreversibly altered upon actuation to restrict a lancet tip to being used just once.

7. A self-actuating and automatically retracting lancing device for uses comprising pricking a fingertip and other percutaneous puncture sites of a medical patient, said device comprising:
   a lancet housing comprising torsion spring restraining means, torsion spring releasing means, and lancet guide means;
   precocked torsion spring means;
   lancet means comprising sharpened lancet tip and;
   in combination, said housing, spring means and lancet means comprising means for translating rotary motion of said torsion spring means to a desired linear motion for said lancet means through a period while the torsion spring means undergo spring unwinding.

8. A self-actuating and automatically retracting lancing device according to claim 7 wherein said spring means and lancet means are an integral part of the same means formed from one length of stainless steel spring wire having bending points used in translation of spring rotary motion to desired lancet linear motion.

9. A self-actuating and automatically retracting lancing device according to claim 8 wherein bending points on said wire are annealed to form reliable hinges.

10. A combination comprising a plurality of lancing devices, a housing for joining said plurality of lancing devices into a single lancet strip and a carrier for the housing, said combination comprising:
   the housing which comprises:
      means for serially interconnecting a plurality of said lancing devices;
      means for sealing and maintaining said lancing devices in a sterile condition until opened for use;
      at least one means for separating portions of the housing by which said lancing devices can be opened for use and separated from the rest of the housing for disposal after use;
      opposing ends of said housing which aid in maintaining a sealed sterile environment for the lancing devices and at least one of said ends which must be separated from the rest of the housing before a first lancing device can be used;
      each of said lancing devices comprising a lancing part, precocked torsion spring means, means for translating rotary motion of said spring means to desired linear motion of said lancet part, means for discharging said torsion spring means which, when released, dynamically and forcefully fire the lancet outward from the housing by positive spring force and likewise retract the lancet part into the housing for safe disposal while the precocked torsion spring means is releasing energy which has been previously stored in a precocking phase;
   the carrier comprising:
      means for transporting and containing the housing;
      means for precisely positioning said housing and firmly holding the housing during lancing;
      means for actuating the torsion spring discharging means to trigger and thereby fire the lancing part.

11. A combination according to claim 10 wherein said carrier comprises a proximal tunnel end into which said housing is fed and a distal tunnel end where lancet devices are used and frangibly separated.

12. A combination according to claim 10 wherein said positioning means comprise a detent which restricts travel of said housing through said carrier to only one direction.

13. A combination according to claim 10 wherein said carrier comprises a pocket clip means for pocket transport.

14. A combination according to claim 10 wherein said lancing part comprises a frangibly releasable segment and said actuating means comprise a cantilever comprising a raised part positioned to effectively impact against said frangible segment having a length of travel such that the raised part frangibly separates the frangibly releasable segment from the part thereby discharging the torsion spring and activating the lancet part.

15. A combination according to claim 14 wherein said raised part keywise matches the form of the frangible lancet actuation means to provide a measure of safety wherein the likelihood of other means discharging the lancet actuation means is reduced.

16. A method for utilizing a lancet instrument for multiple self-actuating and automatically retracting lancing devices whereby the lancing devices may be individually and sequentially used comprising the following steps:
   providing said lancet instrument comprising a housing for a plurality of said lancing devices and means for frangibly separating the lancing devices which are maintained by the housing in sterile condition before being opened for use, said housing comprising notches to be used with a lancing device positioning means;
   providing a carrier, to enclose and hold said housing, comprising:
      a housing positioning means to position and hold said housing within the carrier such that, prior to use, each lancing device can be firmly held against a puncture site; and
      triggering means to fire the lancet;
   inserting the lancet housing through the carrier until the detent means catches and positions the housing with a frangibly separable segment fully exposed;
   breaking away the frangible separation means to open one aseptic lancing device for use;
   placing the lancing device against the puncture site and activating the triggering means whereupon the puncture site is lanced by release of energy previously stored in a spring, the lancing occurring while the energy is being released, the energy release causing spring motion in a single direction which forces egress/ingress action of said lancing device, said lancet tip being safely restored into the lancing device by constraining spring motion in the same direction.

17. A method according to claim 16 comprising the further step of breaking away a last used lancet device and safely disposing of the last used lancet which is directly and safely disposable because the spent lancet means is wholly returned into the housing at the end of a lancing cycle.

18. Structure for obtaining a droplet blood sample from a medical patient comprising:

lancet means comprising a finger piercing element, an associated potential-energy-storing, biasing element and means associating the piercing element and the biasing element by which a single direction of motion of the biasing element resulting during release of the potential energy is converted to bidirectional substantially linear displacement of the piercing element;

enveloping means substantially encapsulating the finger piercing element therein before and after use, the enveloping means comprising egress/ingress means for the finger piercing element;

actuator means associated with the enveloping means whereby use of the actuator means releases the stored potential energy and initiates the single direction of motion which is translated into said bidirectional displacement whereby the finger piercing element is first caused to forcibly move outward through the egress/ingress means to cause the finger piercing element to pierce a desired body site and to thereafter retract into the enveloping means through the egress/ingress means.

19. Structure according to claim 18 wherein the actuator means comprise a frangible segment of the enveloping means.

20. Structure according to claim 18 wherein the actuator means comprise frangible means by which the one form of motion by the biasing element is manually triggered.

21. Structure according to claim 18 wherein the biasing element comprises a torsion spring.

22. Structure according to claim 21 wherein the torsion spring and the piercing element are integrally connected as one continuous piece.

23. Structure according to claim 21 wherein the torsion spring, the finger piercing element and the motion converting means are formed as one piece.

24. Structure according to claim 18 wherein the motion converting means comprise annealed hinge means.

25. Structure according to claim 18 wherein the biasing means comprises a coiled spring and the motion converting means comprises hinge means comprising two spaced pivot sites whereby same direction rotational unwinding of the coiled spring twice bi-pivots the hinge means to extend and then retract the piercing element.

26. Structure according to claim 18 wherein the biasing element and the piercing element are formed as one piece.

27. Structure according to claim 18 wherein the egress/ingress means comprises a port initially closed as a part of a hermetic seal.

28. Structure according to claim 27 wherein the part is manually frangibly removable by a user to expose the port at a desired time.

29. Structure according to claim 18 wherein the biasing means and the finger piercing element comprise separate parts interconnected in cam/cam follower arrangement.

30. Structure according to claim 18 wherein the motion converting means comprise a guide track which obstructs non-linear travel of the piercing element.

31. Structure according to claim 18 wherein the biasing element comprises a coiled spring having a cam end and the piercing element comprises a cam follower slot along which the cam end travels upon actuation of the actuator means.

32. Structure according to claim 18 wherein the biasing means comprise a torsion spring an end of which is anchored against said single direction of motion to the enveloping means at the actuator means whereby actuation of the actuator means releases said end from its anchored condition.

33. Structure according to claim 18 further comprising means for limiting penetration of the piercing means into the body site to a precise predetermined depth.

34. A method of obtaining a droplet of blood sample from a medical patient comprising the steps of:

providing a percutaneous piercing element enclosed within enveloping means comprising an egress/ingress port;

placing the egress/ingress port of the enveloping means at a puncture site of a medical patient;

manually actuating exposed actuator means causing an associated biasing element to be nonlinearly, but unidirectionally displaced;

converting the unidirectional displacement into a first substantially linear displacement of the finger piercing element outward through the egress/ingress port and into the puncture site and thereafter a second opposite substantially linear displacement of the percutaneous piercing element to retract the element entirely within the enveloping means through the egress/ingress port.

35. A method according to claim 34 further comprising the step of manually exposing the egress/ingress port by removal of a portion of a hermetic seal prior to the placing step.

36. A method according to claim 35 wherein the manually exposing step comprises manually breaking a frangible connection disposed distal to a user of the egress/ingress port.

* * * * *